United States Patent
Van Beckhoven et al.

(10) Patent No.: US 7,670,821 B2
(45) Date of Patent: Mar. 2, 2010

(54) METHOD FOR THE PURIFICATION OF MICROBIAL PROTEASE

(75) Inventors: Rudolf Franciscus Wilhelmus Cornelis Van Beckhoven, Breda (NL); Thierry Jean-Bernard Naeye, Toufflers (FR)

(73) Assignee: DSM IP Assets B.V., Heerlen (NL)

( * ) Notice: Subject to any disclaimer, the term of this patent is extended or adjusted under 35 U.S.C. 154(b) by 1111 days.

(21) Appl. No.: 10/515,791

(22) PCT Filed: May 28, 2003

(86) PCT No.: PCT/EP03/05724

§ 371 (c)(1), (2), (4) Date: Nov. 24, 2004

(87) PCT Pub. No.: WO03/100048

PCT Pub. Date: Dec. 4, 2003

(65) Prior Publication Data

US 2005/0153418 A1    Jul. 14, 2005

(30) Foreign Application Priority Data

May 29, 2002    (EP) ................................. 02100578

(51) Int. Cl.
    *C12N 9/50* (2006.01)
(52) U.S. Cl. ..................... 435/219; 435/212; 530/344; 530/350
(58) Field of Classification Search ................ 435/212, 435/213, 219, 220, 223, 224; 530/344
    See application file for complete search history.

(56) References Cited

U.S. PATENT DOCUMENTS

| | | | |
|---|---|---|---|
| 2,683,682 A | | 7/1954 | Miller et al. |
| 3,988,207 A | | 10/1976 | Aunstrup |
| 4,086,139 A | | 4/1978 | Hoerle |
| 4,721,673 A | | 1/1988 | Uren et al. |
| 4,743,551 A | | 5/1988 | Subramanian |
| 5,139,943 A | | 8/1992 | Heinsohn et al. |
| 5,652,348 A | | 7/1997 | Burton et al. |
| 5,856,349 A | * | 1/1999 | Dunlap et al. ............... 514/373 |
| 6,080,758 A | * | 6/2000 | Dodey et al. ................ 514/314 |
| 6,531,485 B2 | * | 3/2003 | Cameron et al. ............ 514/307 |
| 2004/0072320 A1 | * | 4/2004 | Fahrenmark et al. ........ 435/226 |

FOREIGN PATENT DOCUMENTS

| | | |
|---|---|---|
| DE | 280 333 | 7/1990 |
| DE | 43 23 913 | 1/1995 |
| EP | 0 238 023 | 10/2002 |
| EP | 0 700 253 | 5/2003 |
| WO | WO-92/00799 | 1/1992 |
| WO | WO-92/18237 | 10/1992 |
| WO | WO-96/00735 | 1/1996 |
| WO | WO-96/09116 | 3/1996 |
| WO | WO-97/20921 | 6/1997 |
| WO | WO-98/33572 | 8/1998 |
| WO | WO-01/58924 | 8/2001 |
| WO | WO-02/50253 | 6/2002 |

OTHER PUBLICATIONS

Sigma Catalog (1998), p. 1903.*
http://wolfson.huji.ac.il/purification/PDF/HCIC/TOSOH_HIC.pdf; website name only; no paper version is provided.*
Rao et al. "Molecular and Biotechnological Aspects of Microbial Proteases" Microbiol. Molec. Biol. Rev. (Sep. 1998) 62(3): 597-635.*
http://www.cheshiresciences.com/cms/index.php?subcat_id=25&cat_id=4; website name only; no paper version is provided.*
Burton et al., Biotechnology and Bioengineering (1997) 56(1):45-55.
International Search Report for PCT/EP03/05724, mailed on Aug. 20, 2003, 3 pages.
Preetha et al., World Journal of Microbiology and Biotechnology (1997) 13(5):573-578.
Sternberg, J. Dairy Sci. (1971) 54:159-167.
US 5,122,467, 06/1992, Heinsohn et al. (withdrawn)

* cited by examiner

*Primary Examiner*—Sandra Saucier
*Assistant Examiner*—Susan Hanley
(74) *Attorney, Agent, or Firm*—Nixon & Vanderhye P.C.

(57) ABSTRACT

The invention disclose a method for purifying microbial protease, comprising:(i) providing an aqueous liquid sample containing a microbial protease, and a separation medium comprising a base matrix and a plurality of attached ligands that are capable of binding to microbial protease;(ii) contacting separation medium with the sample under conditions permitting binding of microbial protease to the separation medium; and (iii) desorbing microbial protease from the separation medium, wherein the base matrix is hydrophilic and the plurality of ligands are hydrocarbon groups in which all carbon atoms are sp3-hybridised.

38 Claims, No Drawings

METHOD FOR THE PURIFICATION OF MICROBIAL PROTEASE

CROSS-REFERENCE TO RELATED APPLICATIONS

This application is the national phase of PCT/EP03/05724 having an international filling date of 28 May 2003, which claims priority from European application 02100578.0 filed 29 May 2002. The content of these documents are expressly incorporated herein by reference for all purposes.

FIELD OF THE INVENTION

The present invention relates to a method for purifying a microbial proteases and its use to purify milk clotting-enzymes.

BACKGROUND OF THE INVENTION

*Rhizomucor miehei* aspartic protease is a microbial protease suitable for milk-clotting purposes. Preparations of milk-clotting enzymes are used in the food industry, for instance in cheese manufacturing.

*Rhizomucor miehei* aspartic protease is the most commonly used milk-clotting enzyme, due to its low cost and favorable performance (Sternberg, M. Z. (1971) "Crystalline milk-clotting protease from *Mucor miehei*, and some of its properties" *J. Dairy Sci.*, Vol. 54, pp 159-167). This protease can also be produced heterologously via recombinant DNA technology in filamentous fungi (Boel, E. et al. European Patent EP 238 023).

A problem with the production of proteases via microbial fermentation is the expression of other undesirable enzymes. Due to an increasing demand in the market for pure enzyme preparations, several methods have been developed in the art for either the separation and purification of desirable enzymes from enzyme mixtures or for the selective inactivation of undesirable enzymes.

U.S. Pat. No. 2,683,682 (1954) discloses the differential inactivation of proteases or amylases from mixtures of both enzyme types. The method comprises adjusting the pH of the aqueous solution between 3.0 and 4.5 (to selectively inactivate amylase) or between 7.0 and 10.5 (to selectively inactivate protease). The method also comprises maintaining the mixture at a temperature comprised between about 5° C. and 60° C. for a period of time sufficient to inactivate the undesired enzyme, generally for about 0.5 hours or less for higher temperatures and 20 hours for lower temperatures. Treatment of enzyme mixtures derived from malted wheat flour or malted barley at pH 3.6 and 50° C. for 0.5 hours leads to a protease recovery of up to 66% and amylase deactivation of 99.7%. At the same pH but 5° C. for 20 hours the protease recovery is 85%, with an amylase deactivation of 99.6%.

U.S. Pat. No. 4,086,139 (1978) describes the selective inactivation of amylase in enzyme mixtures comprising protease and amylase. The inactivation of amylase occurs by treating the enzyme mixture with an oxidizing agent selected from chlorite and hypochlorite ions. The ions are added to the enzyme mixture in sufficient amount to inactivate the amylase and leave the protease intact, so that further purification steps are avoided. The temperature and pH of the treatment are not critical as far as they are not detrimental to the protease. This method can treat enzyme compositions derived from animal organs (e.g. crude animal organ extracts) or bacteria like *Bacillus subtilis* or *licheniformis* (e.g. fermentation broths). With this method, more than 80% of the amylase is inactivated leaving more than 80% of the protease activity intact.

International Patent Application WO 97/20921 (published Jun. 12, 1997) describes a method for the selective inactivation of at least one undesirable enzyme from an enzyme mixture comprising desirable and undesirable enzymes. The enzyme mixture is treated at a pH lower than 5 and at a temperature from 2 to 75° C. for at least 20 seconds, and/or at a pH higher than 9 and at a temperature from 2 to 75° C. for at least 20 seconds. According to this method, amylase is completely inactivated by treatment of an enzyme mixture comprising amylase and cellulase at pH 3.5 for 1 min at 70° C., while 96% of the cellulase activity remains intact. On the other hand, only 2% of the protease activity is left when enzyme mixture comprising lipase and protease is treated at pH 3.5, 45° C. for 60 minutes. In mixtures comprising cellulase and protease (Example 7), the protease is completely inactivated by treating at 3° C. or 25° C. for 60 minutes and at a pH of 2.5.

U.S. Pat. No. 5,139,943 (1992) describes a method for selective recovery of microbial produced chymosin from mixtures of polypeptides or enzymes produced by fermentation, for example α-amylase. This method is based on the use of a two phase, liquid-liquid system having a partition coefficient for chymosin greater than about 85. The two-phase system is obtained by adding PEG and a salt, for example a phosphate or a sulphate, to the aqueous enzyme composition. The chymosin is selectively extracted into the organic phase while the amylase stays in the aqueous phase. Chymosin can be recovered from the PEG via ion exchange chromatography. By using a pH lower than 3, partition coefficients for chymosin can be obtained of about 1000, allowing full separation from amylase and a chymosin recovery of about 96-98%.

For chymosin obtained by recombinant techniques, U.S. Pat. No. 4,743,551 (Subramanian) and U.S. Pat. No. 4,721,673 (Subramanian et al.) propose dye affinity ligand adsorption and U.S. Pat. No. 5,122,467 (Heinsohn et al.) proposes adsorption to phenyl SEPHAROSE® matrix (SEPHAROSE® matrix is the trade mark of GE Healthcare Biosciences; the corresponding products are based on agarose). U.S. Pat. No. 5,122,467 states that a comparison was made between phenyl SEPHAROSE® matrix and agaroses with other functionalities (including octyl), and it was concluded that only the former provides the required selectivity for chymosin in fermentation broths. Experiments have also been presented to use other ligands containing aromatic rings in WO 96/00735 (Burton et al.) and WO 96/09116 (Burton et al.).

In a recent study by Burton et al. ("One-step purification of chymosin by mixed mode chromatography" in Biotech. Boeing. 56(1) (1997) 4555) a number of chargeable and non-chargeable aromatic ligands have been examined for adsorption of chymosin from a fermentation broth.

Purification of microbial protease can be achieved by binding of microbial protease to an appropriate chromatographic resin. Suitable resins are for instance ion exchange resins. Ion exchange chromatography depends upon the reversible adsorption of charged solute molecules to an immobilized ion exchange group of opposite charge. Separation is obtained because different substances have different degrees of interaction with the ion exchanger due to differences in their charges and charge densities. Molecules are bound to ion exchangers when they carry a net charge opposite to that of the ion exchanger. The binding is electrostatic and reversible. Ion exchange chromatography is a technique which offers different selectivities using either anion or cation exchangers.

Separation can be obtained by differences in charge of the biological compounds. Changing the pH alters the charge characteristics of the sample components and can thus modify the separation.

Anion exchangers, for instance Q-SEPHAROSE® matrix, can be used if a microbial protease solution at a pH above its isoelectric point (IP) is applied to an anion exchanger equilibrated at the same pH. The bound microbial protease can be eluted (desorbed), free of contaminating proteins by increasing the ionic strength and/or changing the pH. The change in ionic strength and/or pH during desorption can take place as a stepwise or continuous gradient.

The same separation can be achieved with a cation exchanger, for instance SP-SEPHAROSE® matrix, if a microbial protease preparation is applied to the resin below its IP.

Other suitable resins are hydrophobic interaction media. Using a hydrophobic interaction medium, separation can be based on the differences in hydrophobicity. Different hydrophobic interaction resins are available containing different ligands for instance ethyl, propyl, butyl, phenyl, and octyl. By applying an aqueous microbial protease solution under conditions permitting binding of microbial protease to the resin, it is possible to separate microbial protease from contamination compounds Some purification methods described in the art have the disadvantage of being laborious. In general, said methods are characterized by a low selectivity towards protease and/or by a relatively high loss in protease activity and/or by excessive use of salts and/or solvents. Despite the number of previously suggested purification protocols, there is still a need for improvements relating to yield/recovery, purity, specific microbial protease activity, simplicity of operation, need for elution agents and salt burden amongst others.

SUMMARY OF THE INVENTION

The present invention provides a method for purifying microbial protease comprising the steps of:

A method for purifying microbial protease, comprising:
 (i) providing an aqueous liquid sample containing a microbial protease, and a separation medium comprising a base matrix and a plurality of attached ligands that are capable of binding to microbial protease;
 (ii) contacting separation medium with the sample under conditions permitting binding of microbial protease to the separation medium; and
 (iii) desorbing microbial protease from the separation medium, wherein the base matrix is hydrophilic and the plurality of ligands are hydrocarbon groups in which all carbon atoms are sp$^3$-hybridised.

Further the present invention provides a method for purifying microbial protease comprising the steps of:

A method for purifying microbial protease comprising the steps of:
 (i) providing an aqueous liquid sample containing microbial protease and a separation medium comprising a hydrophilic base matrix;
 (ii) contacting the separation medium with the sample under conditions permitting binding of microbial protease to the separation medium; and
 (iii) desorbing microbial protease from the separation medium;

wherein the separation medium has a hydrophilic/hydrophobic balance that in the test given in the experimental part gives a retention time (r) for α-chymotrypsinogen which is within the interval $r_{standard} \pm 50\%$ where $r_{standard}$ is the retention time for α-chymotrypsinogen on variant B of n-butyl-OCH$_2$CH(OH)CH$_2$-SEPHAROSE FAST FLOW® matrix, with preference for said retention time (r) being within the interval: standard ±10%.

DETAILED DESCRIPTION OF THE INVENTION

The term "microbial protease" means a protease of microbial origin.

The term "*Rhizomucor miehei* aspartic protease" means the aspartic protease homologously produced in Rhizomucor miehei. A process for the preparation of the enzyme via fermentation is described in U.S. Pat. No. 3,988,207. The term "*Rhizomucor miehei* aspartic protease" also means a recombinant *Rhizomucor miehei* aspartic protease, for example a *Rhizomucor miehei* aspartic protease produced in a host organism (e.g. other than *Rhizomucor miehei*) transformed with DNA coding for the *Rhizomucor miehei* aspartic protease. The host organism can be a fungus, e.g. yeast or a filamentous fungus. Preferably the host organism is a filamentous fungus selected from the genera of *Aspergillus, Trichoderma, Penicillium, Fusarium* or *Humicola*. Most preferably, the filamentous fungus belongs to the genera *Aspergillus* or *Trichoderma*. The use of *Aspergillus niger, Aspergillus nidulans* or *Aspergillus oryzae* as a host strain is preferred. A method for the production of a recombinant *Rhizomucor miehei* aspartic protease in a host organism is described in European Patent Publication EP 0 700 253 A1.

The term "*Rhizomucor miehei* aspartic protease solution" means a solution comprising *Rhizomucor miehei* aspartic protease. Said solution is preferably aqueous.

Similar definitions as above apply for the terms "*Rhizomucor pussilus* aspartic protease" and "*Rhizomucor pussilus* aspartic protease solution" mutatis mutandis.

The method of the invention can be advantageously applied to microbial proteases such as *Rhizomucor miehei* aspartic protease or *Rhizomucor pussilus* aspartic protease derived from fermentation broths or derivatives thereof obtainable at any one of the stages during the down-stream process, generally before the formulation step. The *Rhizomucor miehei* aspartic protease solution is preferably a fermentation broth, most preferably a fermentation broth derived from the fermentation of *Rhizomucor miehei*, which can be obtained according to methods known in the art, for example like described in "Pilot plant experiment" of the U.S. Pat. No. 3,988,207. In another preferred embodiment of the invention, the fermentation broth is a fermentation broth of a host organism transformed with DNA coding for the *Rhizomucor miehei* aspartic protease and expressing the enzyme. Generally, the *Rhizomucor miehei* aspartic protease solution can be obtained from the fermentation broth after removal of the cells. The latter may be achieved by killing of the microorganisms in the fermentation broth by one of the several methods known in the art and by removal of the cell debris. Removal of the cells can be achieved by one or more solid/liquid separation techniques like flocculation, centrifugation, filtration, and membrane separation. Generally, the *Rhizomucor miehei* aspartic protease solution is obtained from the fermentation broth after removal of the cells and concentration prior to use in the method of the invention. Concentration may be achieved by evaporation or membrane concentration; preferably the membrane concentration is achieved by ultra filtration techniques. Therefore in a preferred embodiment of the invention the *Rhizomucor miehei* aspartic protease solution is a cell-free and/or concentrated fermentation broth. The term "cell-free" means that the solution is free of any particle or cell with diameter of 0.4 µm or higher. Similar embodiments as outlined above apply for *Rhizomucor pussilus* aspartic protease.

An objective of the invention is to provide adsorption/desorption protocols for microbial protease, which results in improvements relating to at least one of yield/recovery, purity, specific microbial protease activity, simplicity of operation, need for elution agents and salt burden amongst others.

An improvement may relate to the adsorption/desorption step as such or to the overall process. In other words an increase in purity in the adsorption/desorption step can imply that a preceding step normally carried out may be unnecessary.

The present inventors have found that at least one objective can be at least partially achieved if the ligands are non-aromatic hydrocarbon groups. This is contrary to what has been suggested in U.S. Pat. No. 5,122,467 (Heinsohn et al.).

The first aspect of the invention is a method for purifying microbial protease, comprising:
(i) providing an aqueous liquid sample containing a microbial protease, and a separation medium comprising a base matrix and a plurality of attached ligands that are capable of binding to microbial protease;
(ii) contacting separation medium with the sample under conditions permitting binding of microbial protease to the separation medium; and
(iii) desorbing microbial protease from the separation medium, wherein the base matrix is hydrophilic and the plurality of ligands are hydrocarbon groups in which all carbon atoms are $sp^3$-hybridised.

The hydrocarbon groups in the ligands may or may not be identical, they may be straight, branched or cyclic. They may contain 1-30 carbon atoms, typically 3-25 carbon atoms. In the hydrocarbon groups, an ether oxygen atom (—O—) or a thioether sulphur atom (—S—) may have been inserted between two carbon atoms at one or more positions in at least one of the hydrocarbon groups that is present in the separation medium used. A hydrogen atom that binds to a carbon atom may have been replaced with a hydroxyl group at one or more positions. The ratio of the sum of sulphur atoms and oxygen atoms to the number of carbon atoms in each hydrocarbon group is typically <1, with preference for <0.8 or <0.5 or <0.25.

General stability requirements apply to the hydrocarbon groups, meaning that both an ether oxygen atom and a thio-ether sulphur atom require binding to $sp^3$-hybridized carbon atoms in both directions. Further, $sp^3$-hybridised carbon atoms in a hydro-carbon group should bind to at most one heteroatom selected amongst ether oxygen atoms, hydroxyl oxygen atoms and thioether sulphur atoms. The hydrocarbon group may contain one or more pure alkyl groups including pure alkylene groups, i.e. hydrocarbon groups in which there are only hydrogen atoms and $sp^3$-hybridised carbon atoms. Typical pure alkyl/alkylene groups have 1-12 carbon atoms, preferably 2-10, such as 3-10, carbon atoms. These alkyl groups may be straight, branched or cyclic.

Typical hydrocarbon groups that may be ligands are:
Pure alkyl groups as discussed above. Illustrative examples are methyl, ethyl, n-propyl, isopropyl, n-butyl, sec-butyl, tert-butyl, various isoforms of pentyl, hexyl, heptyl, octyl etc. For pentyl and higher homologues the groups may contain cyclic structures.

Hydrocarbon groups that are obtainable by hydroxy alkylation of a base matrix, e.g. 2-hydroxy alkyl groups.

Hydrocarbon groups that are obtainable by reacting a base matrix with dialkyl ethers in which one or both of the alkyl groups contains an epoxy group, for instance the use of glycidyl alkyl ether for insertion of the group —[CH$_2$CH(OH)CH$_2$O]$_m$R where R is a pure alkyl group containing a cyclic structure ($C_nH_{2n-1}$) or only a straight and/or branched structure ($C_nH_{2n+1}$) and m and n are integers $\geq 1$.

The ligands are preferably hydrocarbon groups comprising three, four or five carbon atoms, more preferably four carbon atoms.

In addition to ligands comprising the above-defined hydrocarbon groups there may also be other kinds of ligands in the separation medium.

The ligands/hydrocarbon groups may or may not have been immobilized to the base matrix via a spacer. In the context of the invention, the spacer is considered to start at the base skeleton of the base matrix and ends after (a) the last heteroatom that is not a thioether atom or an ether atom, or (b) the last sp- or $sp^2$-hybridised carbon atom, which is part of the chain linking the ligand to the base matrix. If every heteroatom is an ether oxygen atom or a thioether sulphur atom and every carbon atom is $sp^3$-hybridised, there is no spacer (the ligand is attached directly to the base matrix).

The spacer, if present, thus may comprise groups selected from ether groups, thioether groups, bivalent hydrocarbon groups, ester groups, amide groups, azo groups and sulphone groups amongst others, as well as those known in the field. The only proviso is that the terminal of the spacer, which is distal to the base matrix, cannot be an ether atom or a thioether atom or an $sp^3$-hybridized carbon atom. A bivalent hydrocarbon group in a spacer has a chain of $sp^3$-hybridised carbons that may carry uncharged or unchargeable substituent groups and may contain straight, branched or cyclic structures. Amide groups may be N-substituted with alkyl, which possibly in turn is substituted with one or more hydroxy groups, as described for hydrocarbon groups above.

In the same separation medium the hydrocarbon ligands may or may not be linked to the base matrix via a spacer. There may also be present different spacers as defined above.

In the most typical case the length of the spacer is 1-20 atoms (the chain of atoms between the base skeleton of the base matrix and the ligand). A single heteroatom, such as an ether oxygen atom, which is derived from the base matrix and used to anchor the spacer or the ligand to the base matrix, is part of the base matrix and not of the spacer or ligand.

Normal stability requirement applies to the spacer, for instance at most one heteroatom selected amongst sulphur, oxygen and nitrogen should bind to one and the same $sp^3$-hybridised carbon atom.

The base matrix is based on organic and/or inorganic material. The base matrix is preferably hydrophilic and in the form of a polymer that is insoluble and more or less swellable in water. Hydrophobic polymers that have been derivatized to become hydrophilic are included in this definition. Suitable polymers are polyhydroxy polymers, e.g. based on polysaccharides, such as agarose, dextran, cellulose, starch and pullulan amongst others; completely synthetic polymers, such as polyacrylic amide, polymethacrylic amide, poly(hydroxyalkylvinyl ethers), poly(hydroxyalkylacrylates) and polymethacrylates (e.g. polyglycidylmethacrylate); polyvinylalcohols; polymers based on styrenes and divinylbenzenes; and copolymers in which two or more of the monomers corresponding to the above-mentioned polymers are included. Polymers, which are soluble in water, may be derivatized to become insoluble, e.g. by cross-linking and by coupling to an insoluble body via adsorption or covalent binding. Hydrophilic groups can be introduced on hydrophobic polymers (e.g. on copolymers of monovinyl and divinylbenzenes) by polymerization of monomers exhibiting groups which can be converted to hydroxyl or by hydrophilization of the final polymer, e.g. by adsorption of suitable compounds, such as hydrophilic polymers.

Suitable inorganic materials to be used in base matrices are silica, zirconium oxide, graphite and tantalum oxide amongst others.

The matrix may be porous or non-porous. This means that the matrix may be fully or partially permeable (porous) or completely impermeable to the compound to be removed (non-porous). For preparative processes the pore sizes should be such that the matrix has a Kav which is in the interval 0.10-0.95 for microbial protease, where the subinterval 0.40-0.95 in particular applies to base matrices which are devoid of so-called extenders.

In an interesting embodiment of the present invention, the matrix is in the form of irregular or spherical particles with sizes in the range of 1-1000 µm, preferably 5-50 µm for high performance applications and 50-300 µm for preparative purposes.

An interesting form of matrices has densities higher or lower than the liquid. This kind of matrices is especially applicable in large-scale operations for fluidized or expanded bed chromatography as well as for different batch wise procedures, e.g. in stirred tanks. Fluidized and expanded bed procedures are described in WO 92/18237 (Amersham Biosciences ) and WO 92/00799 (Kem-En-Tek).

The term "a hydrophilic base matrix" in practice means that the accessible surface of the base matrix is hydrophilic in the sense that aqueous liquids penetrate it. Typically the accessible surfaces on a hydrophilic base matrix expose a plurality of polar groups for instance comprising oxygen and/or nitrogen atoms. Examples of such polar groups are hydroxyl, amino, carboxyl, ester and lower alkyl ethers (such as $(-CH_2CH_2O-)_nH$ where n is an integer). Lower alkyl will in general contain less than 10 carbon atoms and has preferably 2 to 6 carbon atoms.

If present, extenders, tentacles and the like as described in WO 9833572 (Amersham Biosciences ) are considered to be part of the base matrix.

Contrary to the findings presented in U.S. Pat. No. 5,122, 467 (Heinsohn et al.), the present inventors have recognized that separation media based on hydrophilic base matrices and the proper hydrophilic/hydrophobic balance that may be caused by the presence of the above-mentioned hydrocarbon groups can be used in improved separation protocols for microbial protease. The binding ability should be sufficient to give a sufficient binding capacity, and binding strength permitting desorption under conditions not causing irreversible denaturation of microbial protease. The ligand n-butyl-$OCH_2CHOHCH_2$— linked to SEPHAROSE FAST FLOW® matrix as described in the experimental part will work well for the less hydrophobic variants B and C while the more hydrophobic variants A will give a lowered yield in the desorption step.

It follows from the preceding paragraph that the efficiency of different separation media will vary with the hydrophilic/hydrophobic balance in the base matrix, with substitution degree of the hydrocarbon groups (ligands) and with the hydrophilic/hydrophobic balance in the ligand (hydrocarbon group). Taking into account the large number of different base matrices available and the large number of different ligands it becomes impossible to give a range for the substitution degree unless a wide interval is set, such as 0-500 or such as 0-100 or 5-500, µmol/ml wet gel. The extreme value 0 µmol/ml wet gel stands for the case where the base matrix as such provides the proper hydrophobic/hydrophilic balance.

In order to determine if a certain separation medium is efficient or optimal for microbial protease purification, we have developed a method for determining the hydrophilic/hydrophobic balance of separation media. The method is described in the experimental part and means that a separation medium is packed in a column where after α-chymotrypsinogen is allowed to pass through under standard conditions. Suitable separation media to be used in the invention are found amongst those media that give a retention time (r) for α-chymotrypsinogen, which is within the interval $r_{standard} \pm 50\%$ where $r_{standard}$ is the retention time for α-chymotrypsinogen on variant B of n-butyl-$OCH_2CH(OH)CH_2$-SEPHAROSE FAST FLOW® matrix described in the experimental part. Optimal variants normally have retention times within the interval: $r_{standard} \pm 10\%$.

A second aspect of the invention is a method for purifying microbial protease comprising the steps of:

A method for purifying microbial protease comprising the steps of:
(i) providing an aqueous liquid sample containing microbial protease and a separation medium comprising a hydrophilic base matrix;
(ii) *contacting the separation medium with the sample under conditions permitting binding of microbial protease to the separation medium; and
(iii) desorbing microbial protease from the separation medium.

In this aspect of the invention the characterizing feature is that the separation medium has a hydrophilic/hydrophobic balance that in the test given in the experimental part gives a retention time (r) for α-chymotrypsinogen which is within the interval $r_{standard} \pm 50\%$ where $r_{standard}$ is the retention time for α-chymotrypsinogen of variant B of n-butyl-$OCH_2CH(OH)$ $CH_2$-SEPHAROSE FAST FLOW® matrix described in the Examples. Optimal variants normally are found amongst those separation media which have retention times within the interval: $r_{standard} \pm 10\%$.

The separation medium used in this aspect of the invention may or may not have ligands and/or spacers as defined for the first aspect of the invention. The base matrix is as defined above for the first aspect. If no ligands of the kind defined above are present the medium always lacks other ligands that comprise an aromatic ring structure.

A typical protocol for promoting adsorption to a hydrophobic interaction resin is applying an aqueous microbial protease solution with non-denaturing pH and a relatively high ionic strength to the resin. The high ionic strength can be obtained by adding salts to the microbial protease solution. Appropriate salts are for instance ammonium sulphate, sodium chloride, sodium sulphate and the like. After the adsorption, decreasing the ionic strength and/or changing the pH can lead to desorption of the microbial protease. The change in ionic strength and/or pH during desorption can take place as a stepwise or continuous gradient.

Other suitable resins are e.g. gel filtration media and hydrophobic charge induction media.

Surprisingly, *Rhizomucor miehei* aspartic protease and *Rhizomucor pussilus* aspartic protease can be purified very efficiently using hydrophobic interaction resins. The adsorption is typically carried out under conditions promoting adsorption, which means using aqueous liquids with non-denaturing pH and a relatively high ionic strength (high conductivity), for instance corresponding to a salt concentration within the interval 0-2 M $Na_2SO_4$. The pH is below or around the IP (4.2) of, in this case, the *Rhizomucor miehei* aspartic protease, preferably between 2.5 and 5.

Even more surprisingly *Rhizomucor miehei* aspartic protease and *Rhizomucor pussilus* aspartic protease can be purified on hydrophobic interaction resins without the addition of salt. By making use of the hydrophobicity of the protein itself it is possible to purify the protease at low conductivities (<5 $mS.cm^{-1}$). The pH is below or around the IP (4.2) of, in this case, the *Rhizomucor miehei* aspartic protease, preferably between 2.5 and 5, more preferably between 2.5 and 4.

After adsorption of the *Rhizomucor miehei* aspartic protease or the *Rhizomucor pussilus* aspartic protease at low pH and low conductivity, changing the pH to 6 leads to desorption of the *Rhizomucor miehei* aspartic protease or the *Rhizomucor pussilus* aspartic protease, respectively.

The ionic strength may have been accomplished by adding water soluble salts for instance salts of the Group IA and II B elements such as chlorides and sulphates amongst others, including also corresponding ammonium salts. Particularly valuable salts in this respect are NaCl, $NH_4Cl$, $Na_2SO_4$ and $(NH_4)_2SO_4$.

Typical buffer substances are water-soluble acetates, citrates, phosphates and in particular sodium phosphates. The proper choice depends on the desired pH.

The preferred protocol is given in the Examples.

The adsorption and/or desorption steps may be carried out as a batch process in which the separation medium is agitated for instance by stirring or by a through-flowing aqueous liquid. Most preferably, the method of the invention is carried out as a chromatographic process, i.e. with the separation media in form of particles/beads that are packed to a bed or fluidized to an expanded bed. For chromatographic processes the separation medium can also be in monolithic form, for instance in form of a plug or a filter.

In preferred variants, the process of the invention is cyclic, i.e. the separation medium is recovered after step (iii) and reused in step (i), possible with a regeneration step and/or cleaning step inserted between step (iii) and step (i) of a subsequent cycle. Regeneration/cleaning solutions typically contain NaOH (for instance >0.1 M, such as 0.5 or 1 M). By including isopropanol it is possible to reduce the NaOH concentration.

For instance, the yield of *Rhizomucor miehei* aspartic protease obtained in the desorption step is typically ≧60 % such as ≧85 % of the total amount of *Rhizomucor miehei* aspartic protease provided in the sample applied. One cannot exclude that the yield can be equal or exceed 90% in this step. The purity of purified *Rhizomucor miehei* aspartic protease is advantageously above 90% on protein (based on peak area determination at 280 mm in the chromatogram) as determined by analysis with the aid of high performance liquid chromatography based on size exclusion (HPLC-SEC, see further the Examples). Preferably the purity is more than 92%, and more preferably more than 95%.

The method of the invention may also comprise additional steps before or after steps (i)-(iii) as described above. Preceding steps includes, for instance, transforming pro-enzyme, pseudo-enzyme to fully active enzyme, precipitation, filtration and other adsorption steps as well known in the field of protein purification. Potential subsequent steps are desalting, polishing steps that typically mean further purification e.g. by affinity adsorption and drying e.g. by lyophilization, spray drying or similar methods.

The invention is illustrated by, and not limited to, the following examples.

EXAMPLES

Example 1

Synthesis of Prototype Separation Media

SEPHAROSE 4 FAST FLOW® matrix (Amersham Biosciences, Sweden; 100 ml) was rinsed on a glass filter funnel with at least 10 gel volumes of distilled water and transferred to a reaction tank. The total volume was adjusted with distilled water according to Table 1 and agitation was started. $Na_2SO_4$ (16.5 g), NaOH 50% (Table 1), and $NaBH_4$ (0.2 g) were added and allowed to dissolve for at least 1 h. The temperature was raised to 50° C. and butyl glycidyl ether was added (Table 1). After 21±4 h at 50±3° C. the temperature was reduced to 22±3° C. Acetic acid was added to obtain a pH of 6±1. The adsorbent was rinsed on a glass filter funnel with at least 2 gel volumes of distilled water, 6 gel volumes of ethanol and finely with 10 gel volumes of distilled water. The media were stored in 20% ethanol.

TABLE 1

| Prototype | Total volume (ml) | NaOH 50% (g) | Butyl glycidyl ether (g) |
|---|---|---|---|
| A | 120 | 34 | 23.0 |
| B | 133 | 29 | 16.7 |
| C | 125 | 32 | 18.0 |

Example 2

Testing for Hydrophobic/Hydrophilic Balance

Adsorption buffer: 0.02 M tris-(hydroxymethyl)aminomethane +1.70 M ammonium sulphate, adjusted to pH 7.5±0.1 with hydrochloric acid. Elution buffer: 0.02 M tris-(hydroxymethyl)aminomethane adjusted to pH 7.5±0.1 with hydrochloric acid. Sample: α-chymotrypsinogen 1.0 $mg.ml^{-1}$; the protein is dissolved in adsorption buffer.

Column packing: wash approximately 25 ml gel on a glass filter funnel with 250 ml distilled water, and then with 100 ml desorption buffer in small portions. Pack 10 ml gel in each column with a flow rate of 2 $ml.min^{-1}$ and adjust the bed height to 10.5-11.0 cm. Mount the top adaptor and pack for an additional 20 minutes with a flow rate of 4 $ml.min^-$. Mark the bed height during flow, and adjust the top adaptor just below the bed surface. The bed height should now be 10±0.2 cm.

Chromatographic procedure: the test is performed at 23±0.5° C. Equilibrate with 39 ml of adsorption buffer at a flow rate of 1 $ml.min^{-1}$. Inject 1.0 ml of protein mixture with a flow rate of 0.5 $ml.min^{-1}$. Elute the proteins with a gradient, 0-100%, of desorption buffer at a flow rate of 1 $ml.min^{-1}$ for 60 minutes. The retention time is the time from the gradient start until the peek maximum of the proteins is eluted.

All three prototypes were tested according to protocols given above. The test results are given in table 2

TABLE 2

| Prototype | Retention time for α-chymotrypsinogen (min) |
|---|---|
| A | 68 |
| B | 58 |
| C | 62 |

By varying the components in the reaction mixture the same hydrophobic/hydrophilic balance could be obtained by different routes for a given combination of alkyl glycidyl ether and base matrix.

Commercially available octyl SEPHAROSE FAST FLOW® matrix was tested in this method and found to have a retention time of 45±4 min.

Example 3

Chromatographic Experiments with *Rhizomucor miehei* Aspartic Protease

Microbial protease was obtained from a fermentation of the fungus *Rhizomucor miehei*. Approximately 1600 IMCU (International Milk Clotting Unit, definition for bovine rennets by the International Dairy Federation (IDF), protocol 176: 1996)was loaded on a column of 1.2×120 mm packed with butyl SEPHAROSE® 4 FF matrix. A total activity of 30,000 IMCU was applied to a 20 ml butyl SEPHAROSE® 4 FF matrix 16/10 column (diameter 16 mm length 10 cm) at a linear flow rate of 150 cm/hr. The column was equilibrated with 20 mM acetate pH 3. After loading, the column was washed with equilibration buffer containing 200 mM $Na_2SO_4$ at a flow rate of 150 $cm.hr^{-1}$ until the baseline was reached. Elution of the *Rhizomucor miehei* aspartic protease was performed with 20 mM phosphate buffer pH 6. Typically the *Rhizomucor miehei* aspartic protease was eluted as a single peak.

The eluted *Rhizomucor miehei* aspartic protease had a protein purity of 90% based on HPLC-SEC analysis. The process yield was about 90 % on activity (IMCU). Rennet concentration was determined as IMCU. The eluted *Rhizomucor miehei* aspartic protease was free of amylase activity. The amylase activity was determined as RAU. 1 RAU (Amylase activity Unit) is defined as the amount of enzyme that will convert under standardized conditions (pH=6.6, 30° C.) 1 mg soluble starch per minute.

The HPLC-SEC analysis was made on a TSK G 3000 SW, TosoHaas −7.5 mm ID-30 mm, Mobile phase 0.1 M $NaH_2PO_4$, pH 7, flow 1.0 $ml.min^{-1}$.

Example 4

Chromatographic Experiments with *Rhizomucor miehei* Aspartic Protease

Example 3 was repeated except that butyl SEPHAROSE® 6 FF matrix was used. By using butyl SEPHAROSE® 6 FF matrtix less compressibility was found during chromatographic purification of the *Rhizomucor miehei* aspartic protease. The binding capacity was found to be similar as described in Example 3.

Example 5

Chromatographic Experiments with *Rhizomucor miehei* Aspartic Protease

Example 3 was repeated except that different commercial available resins were tested, namely CELLUFINE® butyl matrix(Millipore) and TOYOPEARL® butyl 650 matrix (Toso Haas). In both cases the purity of the resultant *Rhizomucor miehei* aspartic protease was determined to be higher than 90%.

The invention claimed is:

1. A method for purifying *Rhizomucor miehei* aspartic protease or *Rhizomucor pussilus* aspartic protease, comprising:
    (i) providing an aqueous liquid sample comprising a *Rhizomucor miehei* aspartic protease or *Rhizomucor pussilus* aspartic protease, and a separation medium comprising a base matrix and a plurality of attached ligands that are capable of binding to aspartic protease;
    (ii) contacting the separation medium with the sample under conditions permitting binding of the aspartic protease to the separation medium, wherein said conditions comprise a conductivity of <5 $mS·cm^{-1}$; and
    (iii) desorbing the *Rhizomucor miehei* aspartic protease or *Rhizomucor pussilus* aspartic protease from the separation medium;
wherein the base matrix is hydrophilic, the plurality of ligands comprise hydrocarbon groups in which all carbon atoms are $sp^3$-hybridised, and each hydrocarbon ligand is bound to the base matrix (a) by directly attaching said hydrocarbon ligand to an oxygen or sulphur heteroatom that is part of the base matrix, or (b) via a spacer that comprises a bivalent functional group other than ether or thioether in which the functional group is attached directly to one of the hydrocarbon ligands.

2. The method of claim 1, wherein the ligands comprise three, four or five carbon atoms.

3. The method of claim 1, wherein (a) an oxygen or sulphur is inserted between two carbon atoms at one or more positions in at least one of the hydrocarbon groups; or (b) a hydroxy group replaces a hydrogen atom at one or more positions in at least one of the hydrocarbon groups.

4. The method of claim 3, wherein the ratio of the sum of the sulphur and oxygen atoms to the number of carbon atoms in each hydrocarbon group is (i) <1 or (ii) <0.25.

5. The method of claim 1, wherein each of the hydrocarbon groups comprises a $C_{1-12}$ alkyl group.

6. The method of claim 5, wherein the alkyl group comprises a $C_{3-10}$ alkyl group.

7. The method of claim 5, wherein at most one heteroatom selected from the group consisting of sulphur and oxygen is inserted between two carbon atoms in each of the hydrocarbon groups.

8. The method of claim 5, wherein the $C_{1-12}$ alkyl groups are butyl groups.

9. The method of claim 8, wherein the butyl groups are n-butyl groups.

10. The method of claim 1, wherein the conditions permitting binding of the aspartic protease to the separation medium comprise a pH during step (ii) of about or lower than the isoelectric point (IP) of the aspartic protease.

11. The method of claim 1, wherein the yield of aspartic protease in steps (ii)-(iii) is at least 80% of the total amount of aspartic protease provided in step (i).

12. The method of claim 11, wherein the yield of aspartic protease in steps (ii)-(iii) is at least 85% of the total amount of aspartic protease provided in step (i).

13. The method of claim 1, wherein the purity of aspartic protease after steps (ii)-(iii) is at least 90% based on high performance liquid chromatography-size exclusion chromatography (HPLC-SEC) analysis.

14. The method of claim 1, wherein the aspartic protease to be purified is recombinantly produced.

15. The method of claim 1, wherein the base matrix is in the form of porous beads or a porous monolith.

16. The method of claim 15, wherein the surfaces of the pores of the said porous base matrix have a sufficient hydrophilicity for the aqueous liquid to penetrate said pores.

17. The method of claim 1, wherein the base matrix is in the form of beads that in step (ii) form a packed or fluidized bed.

18. The method of claim 1, wherein the method is a chromatographic or batch-wise adsorption process.

19. The method of claim 1, wherein the base matrix comprises a polyhydroxy polymer.

20. The method of claim 19, wherein the polyhydroxy polymer is cross-linked.

21. The method of claim 19, wherein the polyhydroxy polymer comprises a polysaccharide.

22. The method of claim 21, wherein the polysaccharide comprises an agarose, a dextran, a starch, a cellulose or a pullulan.

23. The method of claim 1, wherein the yield of the aspartic protease is at least 85% of the total amount of aspartic protease applied in step (ii) and the purity is at least 90% based on high performance liquid chromatography-size exclusion chromatography (HPLC-SEC) analysis.

24. The method of claim 1, wherein the aspartic protease is a milk-clotting protease.

25. The method to claim 1, wherein the aspartic protease is a *Rhizomucor miehei* aspartic protease.

26. The method of claim 1, wherein the aspartic protease is a *Rhizomucor pussilus* aspartic protease.

27. The method of claim 1, wherein the plurality of ligands comprise hydrocarbon groups which are $C_{4-12}$ alkyl groups.

28. The method of claim 27, wherein the $C_{4-12}$ alkyl groups are butyl groups.

29. The method of claim 28, wherein the butyl groups are n-butyl groups.

30. A method for purifying a *Rhizomucor miehei* aspartic protease or *Rhizomucor pussilus* aspartic protease from a host organism, comprising:
   (i) providing an aqueous liquid sample comprising a *Rhizomucor miehei* aspartic protease or *Rhizomucor pussilus* aspartic protease, and a separation medium comprising a base matrix and a plurality of attached ligands that are capable of binding to the aspartic protease;
   (ii) contacting the separation medium with the sample under conditions permitting binding of the aspartic protease to the separation medium, wherein said conditions comprise a conductivity of <5 mS·cm$^{-1}$; and
   (iii) desorbing the *Rhizomucor miehei* aspartic protease or *Rhizomucor pussilus* aspartic protease from the separation medium;
wherein the base matrix is hydrophilic, the plurality of ligands comprise hydrocarbon groups in which all carbon atoms are sp$^3$-hybridised, and each hydrocarbon ligand is bound to the base matrix (a) by directly attaching said hydrocarbon ligand to an oxygen or sulphur heteroatom that is part of the base matrix, or (b) via a spacer that comprises a bivalent functional group other than ether or thioether in which the functional group is attached directly to one of the hydrocarbon ligands.

31. The method of claim 30, wherein (a) an oxygen or sulphur is inserted between two carbon atoms at one or more positions in at least one of the hydrocarbon groups; or (b) a hydroxy group replaces a hydrogen atom at one or more positions in at least one of the hydrocarbon groups.

32. The method of claim 31, wherein the ratio of the sum of the sulphur and oxygen atoms to the number of carbon atoms in each hydrocarbon group is (i) <1 or (ii) <0.25.

33. The method of claim 30, wherein each of the hydrocarbon groups comprises a $C_{1-12}$ alkyl group.

34. The method of claim 30, wherein the host cell is a fungal cell.

35. A method for purifying a *Rhizomucor miehei* aspartic protease or *Rhizomucor pussilus* aspartic protease from a fermentation broth, comprising:
   (i) providing an aqueous liquid sample from the fermentation broth comprising a *Rhizomucor miehei* aspartic protease or *Rhizomucor pussilus* aspartic protease, and a separation medium comprising a base matrix and a plurality of attached ligands that are capable of binding to aspartic protease;
   (ii) contacting the separation medium with the sample under conditions permitting binding of the aspartic protease to the separation medium, wherein said conditions comprise a conductivity of <5 mS·cm$^{-1}$; and
   (iii) desorbing the *Rhizomucor miehei* aspartic protease or *Rhizomucor pussilus* aspartic protease from the separation medium;
wherein the base matrix is hydrophilic, the plurality of ligands comprise hydrocarbon groups in which all carbon atoms are sp$^3$-hybridised, and each hydrocarbon ligand is bound to the base matrix (a) by directly attaching said hydrocarbon ligand to an oxygen or sulphur heteroatom that is part of the base matrix, or (b) via a spacer that comprises a bivalent functional group other than ether or thioether in which the functional group is attached directly to one of the hydrocarbon ligands.

36. The method of claim 35, wherein (a) an oxygen or sulphur is inserted between two carbon atoms at one or more positions in at least one of the hydrocarbon groups; or (b) a hydroxy group replaces a hydrogen atom at one or more positions in at least one of the hydrocarbon groups.

37. The method of claim 36, wherein the ratio of the sum of the sulphur and oxygen atoms to the number of carbon atoms in each hydrocarbon group is (i) <1 or (ii) <0.25.

38. The method of claim 30, wherein each of the hydrocarbon groups comprises a $C_{1-12}$ alkyl group.

* * * * *